United States Patent [19]

Jacobson et al.

[11] Patent Number: 4,973,560
[45] Date of Patent: Nov. 27, 1990

[54] YEAST STRAINS, METHOD OF PRODUCTION AND USE IN BAKING

[76] Inventors: Gunnard K. Jacobson, 4263 W. Cherrywood La., Brown Deer, Wis. 53209; Nayankumar B. Trivedi, 9485 N. Waverly Dr., Bayside, Wis. 53217

[21] Appl. No.: 818,852

[22] Filed: Jan. 14, 1986

[51] Int. Cl.$^5$ .......................... C12N 1/18; C12N 15/04
[52] U.S. Cl. .................................. 435/256; 435/172.2; 435/942; 426/62; 935/97
[58] Field of Search ...................... 435/256, 942, 172.2; 426/62, 60, 20, 456; 935/97

[56] References Cited

U.S. PATENT DOCUMENTS 4,643,901  2/1987  Jacobson et al. ..................... 426/62

FOREIGN PATENT DOCUMENTS 0128524  12/1984  European Pat. Off. .

*Primary Examiner*—Richard A. Schwartz
*Assistant Examiner*—Richard C. Peet
*Attorney, Agent, or Firm*—Neuman, Williams, Anderson & Olson

[57] ABSTRACT

Novel biologically pure quick acting bakers yeast strains ATCC 20784, ATCC 20785, and ATCC 20786 are provided which show good performance in sweet, regular, and lean doughs, and superior performance in sweet and lean dough, particularly when used in the active dry yeast form. A method of obtaining these and other novel bakers yeast strains by hybridization via protoplast fusion of petite mitochondrial mutants is also provided. Improved methods of baking using these novel bakers yeasts especially in the active dry yeast form are also provided.

12 Claims, No Drawings 4,973,560

1

YEAST STRAINS, METHOD OF PRODUCTION AND USE IN BAKING

BACKGROUND OF THE INVENTION

1. Field of the Invention

This invention relates to improved biologically pure, novel strains of quick acting general purpose bakers yeast which show good performance in sweet and regular dough systems and especially superior performance in sweet doughs, and methods of obtaining the same from existing strains of quick acting bakers yeast by hybridization via protoplast fusion of mitochondrial petite mutants of such quick acting yeast, to quick acting active dry yeast made from these strains yeast and to improved baking methods using said novel yeast strains in active dry yeast form.

2. Description of the Prior Art

The quick acting strains of the yeast *Saccharomyces cerevisiae* are known and are commercially available in active dry yeast form. These yeast are generally characterized by the rapid production of a relatively large amount of carbon dioxide in a given time frame when mixed with doughs which basically contain flour and water, and which usually fall into one of the general categories of sweet, lean or regular doughs. Quick acting yeast are on the average 25% faster than normal dry yeast strains. The value of these so called quick bakers yeasts are especially significant in the commercial baking field particularly when used in the active dry yeast form containing low amounts, i.e., 4 to 8 percent, of moisture. Some of the quick acting yeasts which are available are characterized by a tolerance to sweet doughs which contain substantial amounts of sugar, i.e., up to about 12 to 18% sugar. Generally speaking, these fast acting, or so called quick yeasts of commerce have only moderate activity with a regular or straight dough which contains 4 to 5% sugar and relatively poor activity in lean doughs which contain no added sugar. This recognition has led to commercial yeast producers manufacturing separate yeast products for commercial use in either sweet doughs or lean doughs.

Industrial wild type baking yeast strains, because of their lack of selectable markers cannot be differentiated on laboratory media. That is, upon hybridization of two industrial wild type baking yeast strains no selectable markers are apparent to differentiate the yeast hybrids from the parental strains. Similarly, protoplast fusion of wild type industrial yeast strains has been unsuccessful because fusion products cannot be differentiated from the parental strains. Traditionally, new industrial yeast strains were produced by hybridization. This classical genetic technique uses the yeast cell's natural sexual cycle. Under specific conditions the organism can be made to sporulate. Spore clones of opposite mating type and desired traits can be mated to form a new hybrid yeast. The use of hybridization techniques, however, has been hindered by the fact that many industrial strains have defects in their sexual cycle. Consequently, the genetic content of many strains with desired traits is difficult to recover in spore clones where it can be studied to gain insights into the strains specific characteristics.

The use of recombinant DNA techniques is another way to modify existing industrial yeast strains. Molecular biological manipulation of industrial yeast strains, however, has limited practical uses. Recombinant DNA technology is best suited for the transfer of single gene traits or traits controlled by a small number of genes.

SUMMARY OF THE INVENTION

This invention relates to novel strains of the bakers yeast *Saccharomyces cerevisiae* which are characterized by quick leavening action and particularly by suitability for use in leavening of bakery products made from both sweet or high sugar containing doughs and straight or regular doughs containing 4–5% sugar.

These three commercial novel yeast strains have been deposited in accordance with MPEP § 608.01(p) with the American type culture collection, 12301 Parklawn Drive, Md. 208852-1775. The *Saccharomyces cerevisiae* yeast strains RS 1878, RS 1890 and RS 1909 have been assigned ATCC numbers 20784, 20785, 20786, respectively.

This invention also relates to methods of forming novel hybrids of heterozygotic yeast strains via protoplast fusion of spontaneous petite mutants, i.e., mutations in the mitochondrial genome rather than the nuclear genome, of certain yeast strains and by complementation. Mitocondrial mutants are used because through complementation procedures the hybrid industrial yeast strain can be differentiated from the parent strains. These novel yeast strains are used in the production of active dry yeast for use in the bakery industry, and to improved baking methods using these novel yeast strains in the active dry yeast form.

Broadly, the procedure and method of the present invention involves hybridizing, by protoplast fusion of petite mutants of dissimilar, sexually incompatible, heterozygotic strains of the yeast *Saccharomyces cerevisiae*. More particularly, the process of the present invention involves the steps of (a) growing two dissimilar yeasts on a fermentable sugar-containing culture medium, the said yeast strains being characterized by a relatively high tolerance to sugar and a capacity for proliferative growth on nutrient substrates in which glycerol is the sole carbon source nutrient, (b) isolating spontaneous mitochondrial petite mutant yeast colonies which are characterized by their inability to metabolize glycerol, (c) enzymatically removing the cell wall material to produce yeast protoplasts, (d) hybridizing the yeast by fusing the yeast protoplasts then in the presence of polyethylene glycol, (e) recovering the fused hybridized yeast cells from the fusion step, and (f) growing the protoplast fusion yeast cells on a nutrient substrate with glycerol as the sole carbon nutrient source, and (g) recovering the yeast cells produced by said procedure.

Broadly, the yeast strains used to generate the petite mutants are *Saccharomyces cerevisiae* strains which demonstrate relatively high osmotolerance and relatively quick acting characteristics when placed in dough formulations containing flour, water and sugar. Such yeasts are well known commercially and have also been referred to in the literature—see, e.g., U.S. Pat. No. 3,993,783 which refers to strains Ng 2031 and Ng 2103 and U.S. Pat. No. 3,394,008 which refers to strains Ng 740 and Ng 1777, said accession numbers have been assigned to yeast deposited in the Centraalbureau voor Schimmelcultures, Delft, Netherlands.

Preferably the strains used in the hybridization and protoplast fusion procedure of this invention are also characterized by the fact that the stains cannot mate in nature nor can the mitochondrial petite mutants arising from the culture of said yeast be mated. The yeasts are also characterized by their capacity to grow on substrates in which glycerol is the sole carbon source nutrient.

The two selected yeast strains chosen as petite mutant sources, are first cultivated on nutrient substrates in which a fermentable sugar such as glucose, or in some cases sucrose, is the sole carbon nutrient source. Such growth procedure gives rise to spontaneous mitochondrial petite mutant colonies which are distinguished from the grande colonies by size and color. These colonies are treated with the dye 2, 3, 5-triphenyl tetrazolium chloride (TTC) which stains normal colonies pink while petite colonies remain white.

In a typical procedure, the petite colonies are isolated and sub-cloned on yeast extract, peptone and dextrose media (YPD) plates. The sub-clones are then replicated on yeast extract, peptone, glycerol (YPGLY) plates to confirm and select the desired petite mutants which do not grow on substrates having glycerol as the carbon nutrient source. The selected sub-clone isolates are then separately grown on a YPD liquid broth culture for 48 hours and harvested by separation (centrifugation) from the nutrient media which is washed from the cells. The sub-clone cultures of the petite mutant yeast cells are then treated with an enzyme, $\beta$-glucuronidase, to remove the cell walls thereby creating yeast protoplasts which are thoroughly washed.

The separate yeast protoplasts thus produced from the source yeast petite colonies following this protocol, are then combined and suspended in a fusion buffer of polyethylene glycol (mol. wt. 4000–6000), sorbitol and a calcium salt, and incubated for a period of from 15 to 30 minutes, preferably about 30 minutes, and the fusion buffer is then removed.

The recovered cells are incubated overnight in a recovery broth comprising hypertonic glucose which contains 1% yeast extract, 0.8 molar sorbitol and 0.2% glucose.

Following incubation in recovery broth, the cells were plated on hypertonic glycerol agar which consisted of 1% yeast extract, 2% peptone, 3% glycerol, 0.8 M sorbitol, and 3% agar,. Only fusion products successfully proliferate on glycerol substrates.

The hybrid yeast cells arising on hypertonic glycerol were streaked to YPD, and selected clones were replicated to sucrose, glycerol and sporulation media (potassium acetate) plates. Selected clones which grew on all media were cultured for about 48 hours in a YPD broth. Clones yielding 0.3 grams of yeast solids/100 mL of broth were selected for further evaluation. The selected protoplast fusion yeast hybrids are further selected by gas production (carbon dioxide) tests in three test dough systems for lean and sweet dough activity. Fifty (50) mg (dry weight) of yeast were added to the model mixes shown below. The yeast was suspended in the 15 mL of added water.

| A. | Flour 20 g (4X, Pillsbury) |
| | Water 15 mL |
| B. | Flour 20 g (4X, Pillsbury) |
| | Water 15 mL |
| | NaCl 0.4 g |
| C. | Flour 20 g (4X, Pillsbury) |

| -continued |
| --- |
| Water 15 mL |
| NaCl 0.4 g |
| Sucrose 4 g |

The dough was mixed for 45 to 60 seconds and the mix incubated at 30° C. for four hours, during which the gas volume was measured at half hour (30 min) intervals. Strains which produce more than 300 mL of carbon dioxide per 100 mg yeast solids for test A and at least 200 mL of gas for tests B and C over a four hour test period are selected.

An active dry yeast is readily prepared from these hybrids by standard procedures, i.e., growing the yeast strains in typical multi-stage batch fermentation stages using a molasses as the nutrient carbon source. The yeast harvested from the last or trade fermenter is concentrated and dried under temperature and humidity conditions that maintain its viability, to final moisture contents of between about 4 and 8%, preferably about 6%.

The yeast strain *Saccharomyces cerevisiae* ATCC 20784 has the following physical description:

Cells grown three days at room temperature in 10° Brix malt extract are ovoid to ellipsoidal. The cell size (length $\times$ width) averages $3.6 \times 6.1$ microns. On 1% potassium acetate, 0.1% glucose, 0.25% yeast extract sporulation medium, sporulation efficiency is a poor 1.2%. The frequency of asci with four spores was only 0.3%. Four spored asci are rhomboid or tetrahedral.

The culture ferments $\alpha$-methyglucoside and melezitose slowly. Gas first appears in melezitose and $\alpha$-methylglucoside broth Durham tubes after 3 to 5 days with a standardized 200,000 cell/mL inoculum. Gas production from trehalose was observed after 14–19 days incubation. Protocols used were those of Lodder, North Holland Publishing Co., Amsterdam (1970), pp. 66–73.

The colony morphology on uncrowded (15–30 colonies/plate) Wallerstein's Laboratory (WL) medium after 4 days is pale blue in color, peaked to umbonate in shape with an entire edge. After 10 days on WL medium colonies are smooth with pale blue centers, darker blue toward edges, and pale blue edges. Color sectoring is occasionally seen.

On glycerol medium (uncrowded plates) morphology after 5 days is smooth, convex, with entire edges. After 10 days colony morphology is similar.

A second strain of bakers yeast, ATCC 20785, prepared by the procedure described above. This yeast had similar baking characteristics as ATCC 20784.

This strain is similar in that sporulation is poor—1.4% percent asci and 0.2% percent four spored asci. After 48 hours on 10° Brix malt extract the cells are ovoid to ellipsoidal in shape. Cells average $3.9 \times 5.9$ microns in size.

On uncrowded WL medium after 4 days colonies are peaked to umbonate in shape and pale blue in color. The colony edge is entire. After 10 days on WL color colonies a pale blue with concentrical gradations in color intensity. The colony center tends to be darker in hue and the edges pale. The edge is entire. On glycerol medium after 4 days colonies are smooth, white to creamy, with entire edges and a raised center. After 10 days, the colony adapts a plateau configuration and papillae are seen covering the colony surface and edges.

The strain ferments melezitose and α-methylglucoside slowly. With α-methylglucoside, gas first appears in the Durham tube in 4 days; with α-melezitose, first gas also accumulates after 4 days. Trehalose is fermented poorly with gas being seen only after 14–17 days.

A third strain, ATCC 20786 was isolated. This strain also sporulates poorly—1.0% asci, 0.3% 4-spored asci. The average cell size is 3.6×5.9 microns. Cell shape is ovoid to ellipsoidal.

After 4 days on WL medium colony shape is raised with entire edges; the color is pale blue. After 10 days, colony shape is similar. Color is pale blue in the raised colony center and concentrically darker blue towards the colony edge. The edges are paler in color and entire.

On glycerol medium after 4 days the colony is creamy to white, smooth with entire edges and raised center. After 10 days the colony becomes plateau in shape and papillae cover the surface and edges. Papillation tends to be more common on colonies near the center of the petri dish.

The strain ferments α-methylglucoside, melezitose, and trehalose in the same manner as the previously described strains.

The following examples illustrate the preparation of the novel yeasts of the present invention.

EXAMPLE

Two polyploidal sexually dissimilar strains of quick acting sweet dough yeasts are selected. These strains are characterized by ability to grow on glycerol and by being unable to mate in nature.

The two strains of the yeast *Saccaromyces cerevisiae* were cultivated on a culture media containing 0.3% glucose, 1% potassium acetate, 1% yeast extract, 2% peptone, and 1.5% agar for a period of 4 to 5 days. This plate was overlaid with agar containing 0.067 molar concentration of phosphate buffer, pH, 7.0, containing 0.1% of TTC and 1.5% agar. After an incubation of 4 to 5 hours as indicated above, two types of colonies were produced, namely crande colonies of pink to red coloration and petite colonies of a white color. The petite colonies are considerably smaller than the grande colonies. This follows the protocol as outlined in Science 125, 928 (1957). The petite colonies were removed and streaked for isolation on yeast extract, peptone and dextrose (YPD), a non-selective media, from this, a master plate was formed which was replicated on a YPGLY plate. The pure sub-clone isolates of the original petite cultures which did not proliferate on the glycerol substrate were cultivated in a flask using a YPD broth media for 48 hours and harvested by centrifugation. The yeast cells were washed free of media with water and recovered.

PROTOPLAST FORMATION

The cell concentrations in the suspension were about $5\times10^8$ cells in 2 mL of total volume of solution. The digestion of the yeast cell walls was microscopically followed and when concluded, the protoplasts were washed 5 times with spheroplasting buffer until free of enzyme. $5\times10^8$ yeast cells were incubated for 30 minutes in 0.5 M sodium thioglycollate in a 0.1 M TRIS pH 8.8 buffer. The yeast cells were harvested by centrifugation, washed once, resuspended in 2 mL buffered 1 M sorbitol and 0.1 mL of a 1:10 dilution of β-glucuronidase (Sigma Chemical Co.) was added. Digestion was followed microscopically. After completion (i.e., about 4 hours), the cells were washed 5 times with spheroplasting buffer. The spheroplasting procedure generally follows J. Molec. Bio. 52, 323–335 1970).

The yeasts which were ultimately obtained following the balance of this procedure set out below, were deposited at the American Type Culture Collection and given the accession numbers ATCC 20784, ATCC 20785, and ATCC 20786.

PROTOPLAST FUSION

The protoplasts to be fused were recovered from the cell wall digestion procedures set out above. These protoplasts were mixed in a fusion buffer containing sorbitol (1 M), calcium chloride (0.01 M), and 40% polyethylene glycol having a molecular weight range of 4000 to 6000. The mixture of protoplasts was incubated for 30 minutes, centrifuged and the fusion buffer poured off. The procedure used generally follows *J. Bacteriol.* 130, 946–48 (1977). Recovery broth was added to the recovered fused yeast protoplasts comprising a 1% yeast extract, 0.2% glucose and 0.8 M sorbitol which mixture was incubated overnight (12–18 hours) at a temperature of 30° C.

RECOVERY OF HYBRIDS

Reconstituted fused protoplast yeast cells were plated by pour plate techniques using hypertonic glycerol plating media. Cells were incorporated into a molten agar mixture. The hypertonic glycerol plating media contained 1% yeast extract, 2% peptone, 3% glycerol, 0.8 M sorbitol and 3% agar. The colonies showing growth on the recovery plate represented only the successful fusion products. These were streaked on YPD plates and selected clones replicated to yeast extract, peptone, sucrose media (YPSUC); a sporulation media containing acetate as the carbon source and a YPGLY media. Selected fused protoplast yeast hybrids were innoculated into YPD broth medium and incubated for 48 hours to determine yield. Those yeasts were selected which had a yield of at least 0.3 g (dry weight) of yeast per 100 mL of broth.

RISE TIME SCREENING

After the first screening for yield described above, the yeast hybrid was harvested and subjected to various further gas output measurement screening tests. These tests involved the addition of 50 mg of yeast solids in 15 mL $H_2O$ to various model dough systems. These systems were:

(A) 20 g of Pillsbury (4X) flour, 15 mL of water with yeast.

(B) 20 g of Pillsbury (4X) flour, 15 mL of water with yeast, 0.4 g of NaCl had been added.

(C) 20 g of Pillsbury (4X) flour, 15 mL of water with yeast, 4 g of sucrose, 0.4 g of NaCl.

In all cases the yeast flour and other ingredients were mixed for 45–60 seconds in each test batch.

Gas evolution was measured every ½ hour for a 4 hour period. Only those strains were selected which produced greater than 300 mL of carbon dioxide per 100 mg of yeast solids in rise time test A and 200 mL in rise time tests B and C over the 4 hour test peroid. The procedure and model dough systems are after Harrison and Burrows, J. Inst. Brew. 65, 35–45 (1959).

Novel stains of bakers yeast prepared according to the procedures described above, which passed the gas tests in the model baking dough systems, A, B, and C above, and which yielded 0.3 g yeast/100 mL of broth in growth tests, were propagated in a series of fermenters with a 14 liter last stage fermenter. Molasses yields were 80-85% and considered acceptable. That propagation procedure is set forth in the following example.

MANUFACTURE OF PRESS CAKE YEAST AND ACTIVE DRY YEAST

EXAMPLE

The pure culture of the yeast strain *Saccharomyces cerevisiae* ATTC 20784 was propagated in a series of laboratrory fermenters, the yeast recovered, and reduced in moisture to the cream stage (18-21% solids). Emulsifier (sorbitan monostearate, 1% on yeast solids) or sodium chloride (1-1.5% on yeast solids) was added to the yeast cream which was then reduced to a moisture content of as much as 30 to 90 percent moisture and preferably a moisture content of from about 60% to 70%, particularly 66%, (to form a fresh bakers yeast in a cream, compressed or press cake form) following generally the procedures set forth in Reed and Peppler, *Yeast Technology*, AVI Pub. Co., Westport, Conn. (1973), pp. 83-88.

An active dry yeast is prepared following the procedure generally set forth in Reed and Peppler, Id., pp.90-97.

The fresh bakers yeast press cake (66% moisture) containing surface active agent is extruded as a noodle through a perforated plate (0.02 inch orifices) and dried in a commercially available drier, such as a fluidized bed drier made by Aeromatic Co., Mutenz, Switzerland, under controlled humidity conditions (25 to 60 minutes; 220° F. to 100° F.) to a moisture content of about 4.0 to about 6.5% to produce a high activity active dry yeast (HADY). Usually the yeast used to form the noodle has a moisture content of preferably between about 60-70% or 65 to 70% moisture.

This type of yeast, HADY, can be directly added to the dough without reconstitution in water.

An active dry yeast (ADY) is also prepared by a similar procedure using orifice sizes of about 0.065 inch dried to a moisture content of about 7.4-8.2% based on dry yeast solids. This type of yeast (ADY) should be reconstituted in water before mixing with the dough. The results of the fermentation and drying sequence are set forth in the table below for the three strains of bakers yeast and run by the same procedure as set out below.

TABLE I

| | DRY YEAST DATA | | |
|---|---|---|---|
| Strain | Molasses Yields (%) | % N | % P$_2$O$_5$ |
| ATCC 20784 | 84 | 7.67 | 2.1 |
| ATCC 20785 | 82 | 7.54 | 2.1 |
| ATCC 20786 | 85 | 7.49 | 2.1 |

Bake test showed the following results.

Bake Tests

Bake tests were run on the different yeasts in three different dough systems (i.e., sweet, lean, and regular) using S.J.A. gas measuring equipment. The formulations are as follows:

| REGULAR DOUGH |
|---|
| Premix |
| 500 g flour |
| 20 g sugar |

| -continued |
|---|
| REGULAR DOUGH |
| 20 g non-fat dry milk |
| 10 g salt |
| 15 g shortening |
| Regular Dough Test |
| 500 g of premix (above) |
| 5.5 g of dry yeast |
| 290 mL of 50° F. water |

The test ingredients are mixed in a Hobart Model A-120 mixer for 6 minutes. A 250 g aliquot of dough is placed in the S.J.A. gas measuring equipment maintained at 100.4° F., and the gas evolved is measured at 60 and 90 minute intervals. First rise is considered gas production at 60 minutes. The gas production in the period from 60 to 90 minutes (by difference) is considered proof time for purposes of this test, correlatable with commerical operations. The gas volume units are translated into minutes for first rise and proof time using standard curves derived from actual baking trials. These rise time data correlate excellently to the actual times required to fully leaven a dough in a commercial bakery. Consequently, they are more meaningful than the total volumes of gas produced during the tests.

The same procedure is following in sweet and lean dough systems. The dough formulations and procedure are:

| Sweet Dough |
|---|
| 500 g of premix (above) |
| 72.0 g sugar |
| 11 g dry yeast |
| 250 mL water at 70° F. |

Procedure: Mix for 8 minutes (Hobart), 155 g of dough placed in a S.J.A. apparatus. Measure gas produced at 60 and 120 munite intervals as exemplary of first rise and proof time as described above.

| Lean Dough |
|---|
| 442 g Pillsbury 4X flour |
| 13 g shortening |
| 8.0 g salt |
| 5.5 g dry yeast |
| 300 mL water, 70° F. |

Procedure: Mix in Hobart 6 minutes. Place a 200 g aliquot of dough in S.J.A. apparatus. Readings of gas evolved are taken at 60 and 90 minute intervals as above and converted to minutes for first rise and proof times.

The yeast strains produced in Table I were used in bake tests for regular, sweet, and lean dough systems. The results are shown in Table II below.

TABLE II

| | Rise Times (Min.) | | |
|---|---|---|---|
| YEAST STRAIN | Reg. | Lean | Sweet |
| ATCC 20784 | 122 | 140 | 101 |
| ATCC 20785 | 111 | 142 | 95 |
| ATCC 20786 | 113 | 144 | 106 |

Minimum standards for performance based on commercial averages are lean dough-122 min.; regular-140 min.; and sweet-155 min.

A similar yeast propagation fermentation procedure was run in a 200 liter fermentor (Fermatron, New Brunswick Scientific Co.) with strains ATCC 20784 and ATCC 20785. The results obtained, including the bake tests which demonstrate the superior activities of these strains in reference to sweet doughs, are shown in Table III:

TABLE III

| Strain | % Molasses Yield | Dry Yeast Data | | Rise Times (min.) | |
|---|---|---|---|---|---|
| | | % N | % P$_2$O$_5$ | Reg. | Sweet |
| ATCC 20784 | 88.0 | 6.83 | 2.06 | 127 | 98 |
| ATCC 20785 | 85.7 | 6.98 | 1.97 | 113 | 73 |

The foregoing procedures provide methods for producing novel man made sweed dough yeast hybrids which are useful in providing to the baking industry an improved baking procedure, especially when the yeast is marketed in the active dry yeast form. They provide an instant active dry yeast of good activity in regular doughs but show especially superior results in sweet dough systems.

What is claimed is

1. The biologically pure man made bakers yeast *Saccharomyces cerevisiae* strain ATCC 20784, said strain having improved leavening action in sweet or high sugar containing doughs.

2. The biologically pure man made bakers yeast *Saccharomyces cerevisiae* strain ATCC 20785, said strain having improved leavening action in sweet or high sugar containing doughs.

3. The biologically pure man made bakers yeast *Saccharomyces cerevisiae* strain ATCC 20786, said strain having improved leavening action in sweet or high sugar containing doughs.

4. A fresh baker yeast composition obtained form the bakers yeast *Saccharomyces cerevisiae* strain ATCC 20784 containing about 30 to 90% moisture.

5. A fresh bakers yeast composition obtained from the yeast *Saccharomyces cerevisiae* strain ATCC 20785 containing about 30 to 90% moisture.

6. A fresh bakers yeast composition obtained from the yeast *Saccharomyces cerevisiae* strain ATCC 20786 containing about 30 to 90% moisture.

7. Active dry bakers yeast composition obtained from bakers yeast *Saccharomyces cerevisiae* strain ATCC 20784.

8. Active dry bakers yeast composition obtained from bakers yeast *Saccharomyces cerevisiae* strain ATCC 20785.

9. Active dry bakers yeast composition obtained from bakers yeast *Saccharomyces* cerevisiae strain ATCC 20786.

10. The man made bakers yeast strain *Saccharomyces cerevisiae* ATCC 20784, having improved leavening action in sweet or high sugar containing doughs, made by the protoplast fusion and complementation of spontaneous petite mutant yeast colonies from dissimilar industrial heterozygotic yeast strains of *Saccharomyces cerevisiae* which comprises:

(a) growing yeast strains on a fermentable sugar containing culture medium, said yeast strains being characterized by a relatively high tolerance to sugar and a capacity for proliferative growth on nutrient substrates in which glycerol is the sole carbon source nutrient, (b) isolating spontaneous mitochondrial petite mutant yeast colonies which are characterized by their inability to metabolize glycerol, (c) enzymatically removing the cell wall material to produce yeast protoplasts, (d) hybridizing the yeast by fusing the yeast protoplasts then in the presence of polyethylene glycol, (e) recovering the fused hybridized yeast cells from the fusion step, (f) growing the protoplast fusion yeast cells on a nutrient substrate with glycerol as the sole carbon nutrient source, (g) screening said protoplast fusion yeast cells to select yeasts which proliferate on both glycerol and sucrose nutrient substrates, (h) screening said yeast cells to select yeasts which pass the gas producing tests A, B, C as described herein, and, (i) recovering the yeast cells produced by said procedure.

11. The man made bakers yeast strain *Saccharomyces cerevisiae* ATCC 20785, having improved leavening action in sweet or high sugar containing doughs, made by the protoplast fusion and complementation of spontaneous petite mutant yeast colonies from dissimilar industrial heterozygotic yeast strains of *Saccharomyces cerevisiae* which comprises:

(a) growing yeast strains on a fermentable sugar containing culture medium, said yeast strains being characterized by a relatively high tolerance to sugar and a capacity for proliferative growth on nutrient substrates in which glycerol is the sole carbon source nutrient, (b) isolating spontaneous mitochondrial petite mutant yeast colonies which are characterized by their inability to metabolize glycerol, (c) enzymatically removing the cell wall material to produce yeast protoplasts, (d) hybridizing the yeast by fusing the yeast protoplasts then in the presence of polyethylene glycol, (e) recovering the fused hybridized yeast cells from the fusion step, (f) growing the protoplast fusion yeast cells on a nutrient substrate with glycerol as the sole carbon nutrient source, (g) screening said protoplast fusion yeast cells to select yeasts which proliferate on both glycerol and sucrose nutrient substrates, (h) screening said yeast cells to select yeasts which pass the gas producing tests A, B, C as described herein, and, (i) recovering the yeast cells produced by said procedure.

12. The man made bakers yeast strain *Saccharomyces cerevisiae* ATCC 20786, having improved leavening action is sweet or high sugar containing doughs, made by the protoplast fusion and complementation of spontaneous petite mutant yeast colonies from dissimilar industrial heterozygotic yeast strains of *Saccharomyces cerevisiae* which comprises:

(a) growing yeast strains on a fermentable sugar containing culture medium, said yeast strains being characterized by a relatively high tolerance to sugar and a capacity for proliferative growth on nutrient substrates in which glycerol is the sole carbon source nutrient, (b) isolating spontaneous mitochondrial petite mutant yeast colonies which are characterized by their inability to metabolize glycerol, (c) enzymatically removing the cell wall material to produce yeast protoplasts, (d) hybridizing the yeast by fusing the yeast protoplasts then in the presence of polyethylene glycol, (e) recovering the fused hybridized yeast cells from the fusion step, (g) growing the protoplast fusion yeast cells on a nutrient substrate with glycerol as the sole carbon nutrient source, (g) screening said protoplast fusion yeast cells to select yeasts which proliferate on both glycerol and sucrose nutrient substrates, (h) screening said yeast cells to select yeasts which pass the gas producing tests A, B, C as described herein, and, (i) recovering the yeast cells produced by said procedure.

* * * * *